(12) United States Patent
Keady

(10) Patent No.: US 9,138,353 B2
(45) Date of Patent: Sep. 22, 2015

(54) EARPLUG AND PUMPING SYSTEMS

(75) Inventor: John P. Keady, Fairfax Station, VA (US)

(73) Assignee: Personics Holdings, LLC, Boca Raton, FL (US)

( * ) Notice: Subject to any disclaimer, the term of this patent is extended or adjusted under 35 U.S.C. 154(b) by 180 days.

(21) Appl. No.: 13/201,308

(22) PCT Filed: Feb. 16, 2010

(86) PCT No.: PCT/US2010/024308
§ 371 (c)(1),
(2), (4) Date: Jan. 19, 2012

(87) PCT Pub. No.: WO2010/094033
PCT Pub. Date: Aug. 19, 2010

(65) Prior Publication Data
US 2012/0103346 A1    May 3, 2012

Related U.S. Application Data

(60) Provisional application No. 61/152,545, filed on Feb. 13, 2009.

(51) Int. Cl.
*A61F 11/10* (2006.01)
*A61F 11/08* (2006.01)
*A61F 11/00* (2006.01)

(52) U.S. Cl.
CPC .............. *A61F 11/10* (2013.01); *A61F 11/00* (2013.01); *A61F 11/08* (2013.01)

(58) Field of Classification Search
CPC ........... A61F 11/00; A61F 11/08; A61F 11/10
USPC .......... 128/864, 866–867; 181/129, 135, 130; 381/328, 381, 329
See application file for complete search history.

(56) References Cited

U.S. PATENT DOCUMENTS

| | | | |
|---|---|---|---|
| 2,824,558 A | | 2/1958 | Michael |
| 2,876,767 A | | 3/1959 | Wasserman |
| 3,110,356 A | * | 11/1963 | Mendelson ................... 181/130 |
| 3,505,999 A | | 4/1970 | Harvey et al. |
| 3,602,654 A | | 8/1971 | Victoreen |
| 4,060,080 A | | 11/1977 | Akiyama |
| 4,089,332 A | | 5/1978 | Rose |
| 4,133,984 A | | 1/1979 | Akiyama |
| 4,245,639 A | * | 1/1981 | La Rosa ..................... 604/97.02 |
| 4,834,211 A | | 5/1989 | Bibby |

(Continued)

OTHER PUBLICATIONS

International Search Report for International Patent Appln. No. PCT/US10/24308, mailed Mar. 5, 2012.
Written Opinion for International Patent Appln. No. PCT/US10/24308, mailed Mar. 5, 2012.

*Primary Examiner* — Alireza Nia
*Assistant Examiner* — Camtu Nguyen
(74) *Attorney, Agent, or Firm* — Pablo Meles

(57) ABSTRACT

An earplug is provided. The earplug includes at least a partially flexible distal end; an inflatable element; and a flexible anti-distal end. The anti-distal end has at least one portion that is deformable. The inflatable element is operatively attached to the distal end by an inflation channel. When the at least one portion is deformed the inflatable element expands to an adjustable pressure. At least one portion of the anti-distal end provides a pressurizing force to maintain the expansion of the inflatable element.

5 Claims, 5 Drawing Sheets

(56) References Cited

U.S. PATENT DOCUMENTS

| | | |
|---|---|---|
| 4,896,679 A | 1/1990 | StPierre |
| 4,913,165 A | 4/1990 | Fishgoyt |
| 5,483,027 A * | 1/1996 | Krause .......................... 181/135 |
| 6,256,396 B1 * | 7/2001 | Cushman ...................... 381/328 |
| 6,513,621 B1 | 2/2003 | Deslauriers et al. |
| 2008/0314393 A1 | 12/2008 | Purcell et al. |
| 2009/0173353 A1 * | 7/2009 | Purcell et al. ................. 128/865 |

* cited by examiner

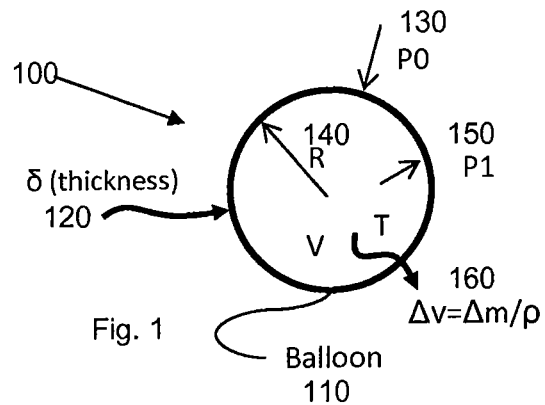
Fig. 1
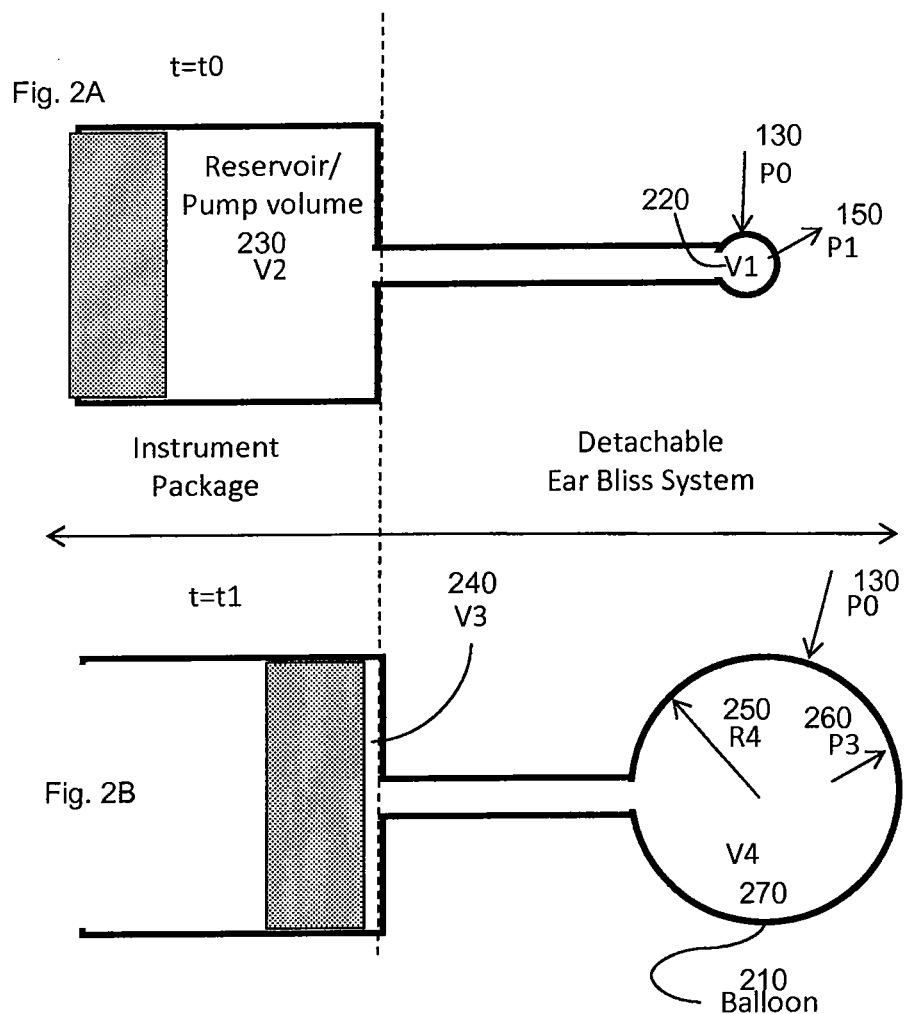
Fig. 2A
Fig. 2B

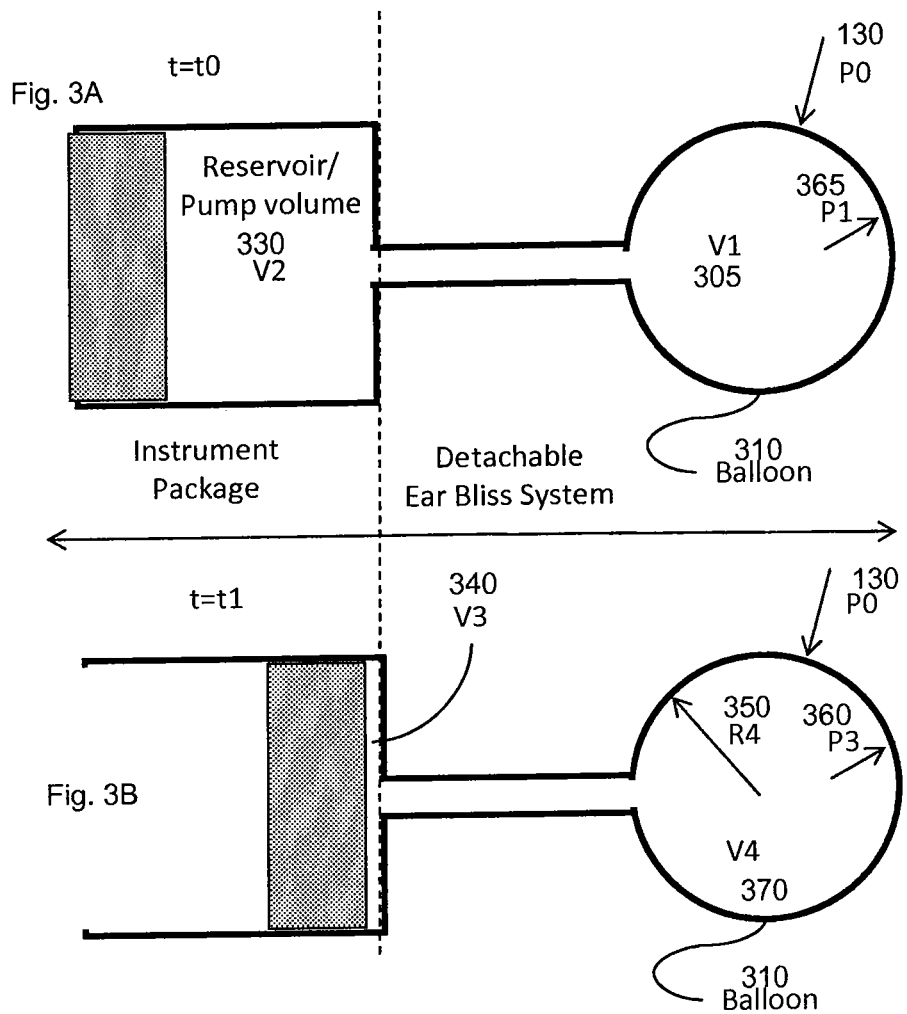

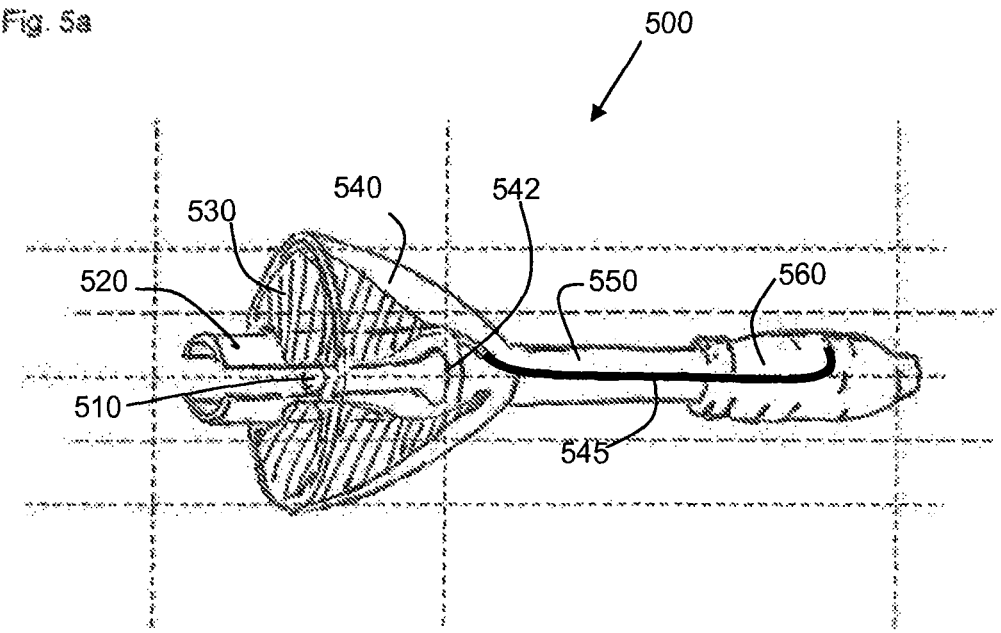
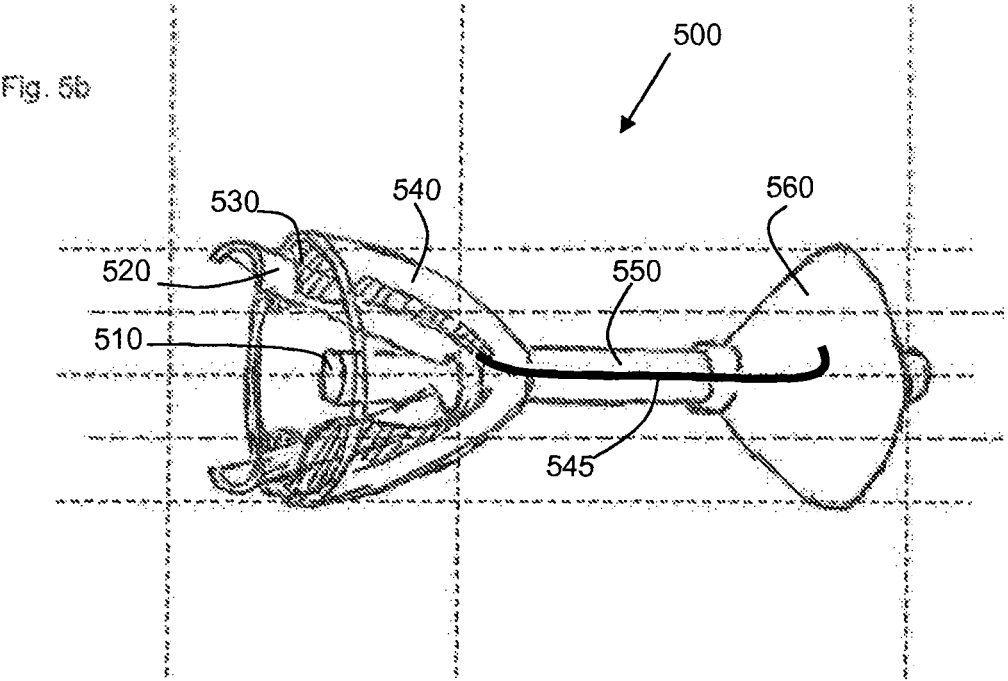

EARPLUG AND PUMPING SYSTEMS

CROSS-REFERENCE TO RELATED APPLICATIONS

This application is a U.S. National Phase Application of PCT International Application No. PCT/US2010/024308 filed Feb. 16, 2010 which claims the benefit of U.S. provisional patent application No. 61/152,545 filed on Feb. 13, 2009, the disclosure of which is incorporated herein by reference in its entirety.

FIELD OF THE INVENTION

The invention relates in general to devices and methods of earphone, earpiece, earbud, fit and sealing technology, and particularly though not exclusively, is related to earplug and pumping systems for earplugs.

BACKGROUND OF THE INVENTION

Earplugs are currently rated with an EPA governed Noise Reduction Rating (NRR). The Noise Reduction Rating (NRR) is the measurement, in decibels, of how well a hearing protector reduces noise as specified by human subject testing as regulated by the Environmental Protection Agency. The higher the NRR number the greater the noise reduction.

Earplug fit affects the effective noise reduction ratio of an earplug. For example one study illustrated that a good fit of the earplug has an NRR of 33 dB, while the same earplug fitted poorly provided an NRR of 0 dB.

In the industrial noise environment the use of hearing protection is paramount. The correct fit of the hearing protection often determines its usefulness. Thus the fit of an earplug is important. Current earplugs have various levels of ease of fit. Professional training can increase the effectiveness of earplug fit, however many users do not have access to professional training. Thus a system that improves the chance of improved fitting will be beneficial to protecting hearing in many users.

Several systems have been developed in the past. For example: Wasserman (U.S. Pat. No. 2,876,767) illustrates (FIG. 7, U.S. Pat. No. 2,876,767) a system requiring an external pump to inflate an inflatable bladder as does Pierre (FIG. 5, U.S. Pat. No. 4,896,679); Rose (U.S. Pat. No. 4,089,332, FIGS. 1-2) illustrates an earplug 10 with a first end 14, that when deformed into a second stable position results in the extension of a second end, the system lacking a method for maintaining a pressurizing force, thus lending itself to possible de-inflation; Krause (U.S. Pat. No. 5,483,027) illustrates a bi-directionally inserted earplug with a two-way valve to maintain a chamber in an expanded condition, while Michael et al. (U.S. Pat. No. 2,824,558) illustrates an earplug with a one-way valve.

Unlike related art, a simplified system (for ease of adoption) designed for use in a particular and adjustable pressure range to provide the necessary sound isolation would be useful.

SUMMARY OF THE INVENTION

At least one exemplary embodiment is related to an earplug comprising: at least a partially flexible distal end; an inflatable element; and a flexible anti-distal end, where the anti-distal end has at least one portion that is deformable, where the inflatable element is operatively attached to the distal end by an inflation channel, where when the at least one portion is deformed the inflatable element expands to an adjustable pressure, where at least one portion of the anti-distal end provides a pressurizing force to maintain the expansion of the inflatable element.

At least one exemplary embodiment provides the pressurizing force using an elastic membrane.

At least one exemplary embodiment provides the pressurizing force using a plate secured by screwing in the plate to a given position.

At least one exemplary embodiment provides the pressurizing force using a resilient member.

Further areas of applicability of embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of the present invention will become more fully understood from the detailed description and the accompanying drawings, wherein:

FIG. 1 illustrates a generic illustration of an inflatable element;

FIGS. 2A and 2B illustrate a generic variable volume inflatable element attached to a reservoir and a stent;

FIGS. 3A and 3B illustrate a generic constant volume inflatable element attached to a reservoir and a stent;

FIGS. 5a and 5b illustrate an earplug including an inflatable element attached to a reservoir and a stent, using a pinchable resilient member to provide a pressurizing force in accordance with at least one exemplary embodiment.

DETAILED DESCRIPTION OF EXEMPLARY EMBODIMENTS OF THE PRESENT INVENTION

Figure 4A:
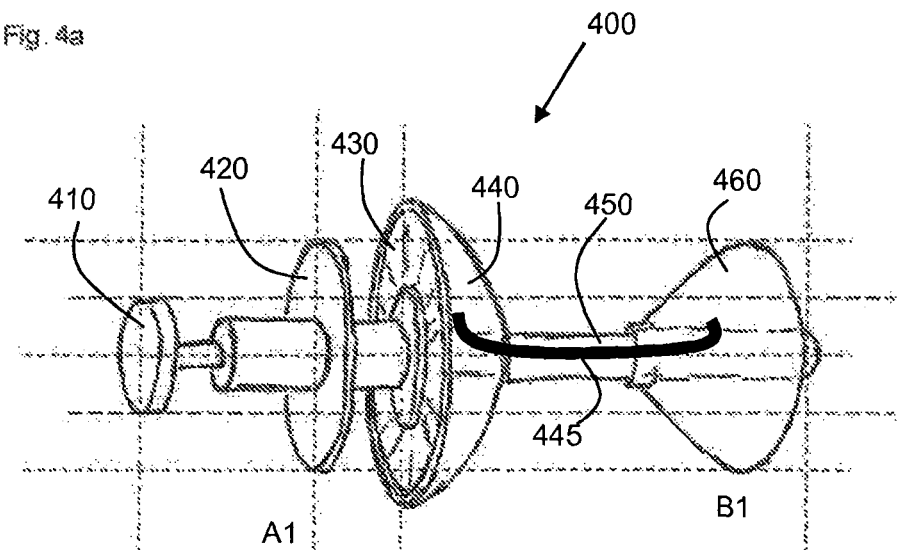
FIGS. 4a and 4b illustrate an earplug including an inflatable element attached to a reservoir and a stent, where an elastic membrane provides a pressurizing force in accordance with at least one exemplary embodiment.

The following description of exemplary embodiment(s) is merely illustrative in nature and is in no way intended to limit the invention, its application, or uses.

Processes, methods, materials and devices known by one of ordinary skill in the relevant arts may not be discussed in detail but are intended to be part of the enabling discussion where appropriate. For example material used for flexible members of various durometer, elastic membrane material, balloon material, may not be specified but are known by one of ordinary skill by earpiece, hearing aid, earplug, and medical angioplasty manufacturers.

Additionally, the size of structures used in exemplary embodiments are not limited by any discussion herein (e.g., the sizes of structures can be macro (millimeter, centimeter, meter, size), micro (micro meter), nanometer size and smaller), and can be used in various orifices besides ear canals although ear canals will be discussed.

The materials used for earplug construction will not be discussed in detail, however any materials, as known by one of ordinary skill in the art of earplug manufacturing and medical balloon manufacturing, can be used to fabricate earplugs in accordance with exemplary embodiments of the present invention. For example Lucite, ultraviolet resin, polyethylene, soft acrylic, soft ultra-violet silicone, polyvinyl chloride, medical polymers, foam, can all be used for various portions of the earplug construction.

At least one exemplary embodiment is directed to an earplug comprising: at least a partially flexible distal end; an inflatable element; and a flexible anti-distal end, where the anti-distal end has at least one portion that is deformable, where the inflatable element is operatively attached to the distal end by an inflation channel, where when the at least one portion is deformed the inflatable element expands to an adjustable pressure, where at least one portion of the anti-distal end provides a pressurizing force to maintain the expansion of the inflatable element.

The distal end can include a flexible and inflexible portion. The flexible portion can be an elastic membrane for example an elastic membrane that can be stretched to several initial lengths then returned to its original size. Many materials can be used (e.g., silicon) that provide a restoring force when deformed (e.g., stretched). Typically such materials have a lower Durometer (e.g., less than 50 Shore).

The inflexible portion can be made of less stretchable material, for example when stretched to less than 100% the material returns to its shape, for example typically such materials have a higher Durometer (e.g., greater than 50 Shore).

The flexible portion can also be a compressible or expandable bladder operatively attached to the inflexible portion.

The deformable portion of the anti-distal end can be any deformable portion of the anti-distal end for example it can be a bladder, or a deformable dome of the anti-distal end, where deformation moves fluid from one section into the inflatable element.

The inflatable element can be any element that can be inflated for example a self contained bladder or balloon, or a sheath around a stent that can expand away from the stent.

The inflatable element can be operatively attached to the distal end by an inflation channel. The inflation channel can be a tube carrying fluid from the anti-distal end to the inflation element, or can be a channel for example within a stent.

The inflatable element can be pressurized via fluid transfer into the inflatable element. For example deformation of a portion of the anti-distal end moves fluid from a chamber (e.g. a bladder) through an inflation channel into the inflation element. A pressure can be chosen (e.g., by deforming a portion of the anti-distal end by a given amount) for the gauge pressure inside the inflation element. Note that the fluid can be water, air, or any type of fluid and gas that provides the requisite time of pressurization. For example if the inflation element is to be pressurized from 0.3 bar gauge pressure to 0.25 bar gauge pressure for 12 hours, then the material requirement for the inflation element and other pneumatic systems can be determined (e.g., the inflation channel can also be designed to reduce permeability within the given limits). Thus in the non-limiting example above a material can be chosen to provide the necessary permeability for the given fluid used (e.g., Teflon for air for 12 hours or more for an inflation element that maintains gauge pressure from 0.3 bar gauge pressure to 0.25 bar gauge pressure).

In accordance with at least one exemplary embodiment a pressurizing force can be applied to the pneumatic system (e.g., bladder in the anti-distal end, the inflation channel and the inflation element). For example a screwed in plate can press against an anti-distal end bladder deforming it increasing the pressure in the pneumatic system, where the thread force maintains the pressurizing force. Additionally other systems can provide the pressurizing force, for example an elastic membrane can provide a restoring force. For example one can pre-pressurize a closed pneumatic system to the desired gauge pressure, then one end pulled (e.g., a plate attached to an elastic membrane pulled), pulling the fluid out of the inflation element, where when the pulling action is released the elastic membrane provides a restoring force that forces the fluid back into the inflation element.

A further exemplary embodiment can use a resilient member to provide a restoring force when deformed. For example a plastic clip can be pulled then released to return to its original shape. In at least one exemplary embodiment a resilient member in the form of an opened plastic clip presses against a bladder, so that when the plastic clip is pinched it closes around a stent and the bladder is free to fill, which if coupled to an inflation element will inflate the inflation element. The volume of the deformation can be calculated to provide the requisite inflation element pressure.

The inflatable element can be a sheath around a stent, where a hole in the stent allows fluid to flow into the sheath stretching the sheath until the orifice in which the sheath is placed is obstructed or occluded. The inflation element can also be a balloon attached to a stent that is inflated or deflated. The inflation element can be made of various elastic materials. Additionally the inflatable element can be a non-elastic material that is preformed to a size and shape when inflated. For example a variable volume balloon can be tight against the stent when deflated. When inflated it can expand until a predesigned shape is obtained, for example by varying the thickness of the balloon along the stent direction. For example a constant volume balloon can be preformed into a shape (e.g., a cone).

The inflatable element can be pressurized to a range of gauge pressures (pressure difference between inside the inflation element and outside the inflation element). For example the inflatable element can be pressurized to a gauge pressure range between 0.05 bar and 3.0 bar. The pressurized inflation element can provide sound isolation when the inflation element occludes an orifice (e.g., ear canal).

FIG. 1 illustrates a generic illustration of an inflatable element 100 including balloon 110. The permeability $\epsilon$ can be expressed in terms of radius 140 R, the internal pressure 150 P1, the outside pressure 130 P0, the temperature T, the volume V, the change of volume 160 $\Delta v$, the change of mass $\Delta m$, the surface area A, the permeability $\epsilon$, a thickness of a membrane 120 $\delta$ and time t, as:

$$\epsilon = [\Delta v \, \delta]/[At(P1-P0)] \quad (1)$$

For example if air is used, which has a molecular weight of 4.817E-26 Kg/molecule, a density $\rho$ of 1.29 kg/m^3, a temperature of 20 C or 293K, a radius of 7 mm, an internal pressure P1=1.2 atm, and outside pressure of P0=1.0 atm, a surface area of 6.15 cm^2, a thickness of a balloon $\delta$=0.002 inch or 0.005 cm, where the pressure drops from 1.2 atm to 1.0 atm in t=8 hours, a permeability value $\epsilon$ of $$\epsilon = 1.24E\text{-}10 \text{ cm}^3 \text{ cm}/(s \text{ cm}^2 \text{ cmHg}) \quad (2)$$

is obtained. Thus materials that have an equivalent permeability or less will satisfy the design criteria. For example butyl rubber, polystyrene, polyethylene high density, nylon 6, and Teflon and other like materials.

FIGS. 2A and 2B illustrate a generic variable volume inflatable element attached to a reservoir and a stent. FIG. 2A illustrates a non-inflated variable volume balloon having an uninflated volume 220 V1, having an uninflated internal pressure of 150 P1 and an outside pressure of 130 P0. The variable volume balloon can be attached to a reservoir having a pump volume 230 V2. The reservoir can be reduced starting at time t=t0 to a final volume 240 V3 (FIG. 2B) at time t=t1. The decrease of the reservoir volume moves fluid into the variable volume balloon 210, increasing the volume 270 V4, where the radius has increased to 250 R4 and the internal pressure increases to 260 P3. If one assumes an initial volume V1 about 0, V3 about 0, and P1=P0, then one can solve for the volume V4 and the pressure P3 as:

$$V2=(P3*V4)/P1 \quad (3a)$$

$$P3=P1+[(2\sigma)/R4] \quad (3b)$$

Where σ is the surface tension of the expanded inflation element. For example if one wishes to have V4=1000 mm^3, P3=1.2 atm and P0=1.0 atm, then V2=1.2 cm^3.

FIGS. 3A and 3B illustrate a generic constant volume inflatable element attached to a reservoir and a stent. In FIG. 3A, the constant volume inflatable element has an initial volume 305 V1, an internal pressure 365 P1 and an outside pressure 130 P0. At time t=t0, the reservoir has a pump volume 330 V2. The reservoir can be reduced to a final volume 340 V3 at time t=t1 (FIG. 3B). The decrease of the reservoir volume moves fluid into the variable volume balloon 310, increasing the volume 370 V4, where the radius has increased to 350 R4 and the internal pressure increases to 360 P3. Assuming that the initial volume 305 V1 is not 0, that 370 V4 is not 0, that 305 V1 is not equal to 370 V4, the reservoir volume 330 V2 can be calculated as:

$$V2=[(P3*V4)/P1]-V1 \quad (4)$$

If one assumes that the balloon 310 (inflatable element) is a constant volume, thus V1 is about =V4, then the reservoir volume needed can be expressed as:

$$V2=[(P3*V4)/P1]-V4 \quad (5)$$

For example if one designs V4=1000 mm^3, an internal pressure of 1.2 atm, an outside pressure of 1.0 atm, one can obtain V2=0.2 cm^3.

Figure 4B:
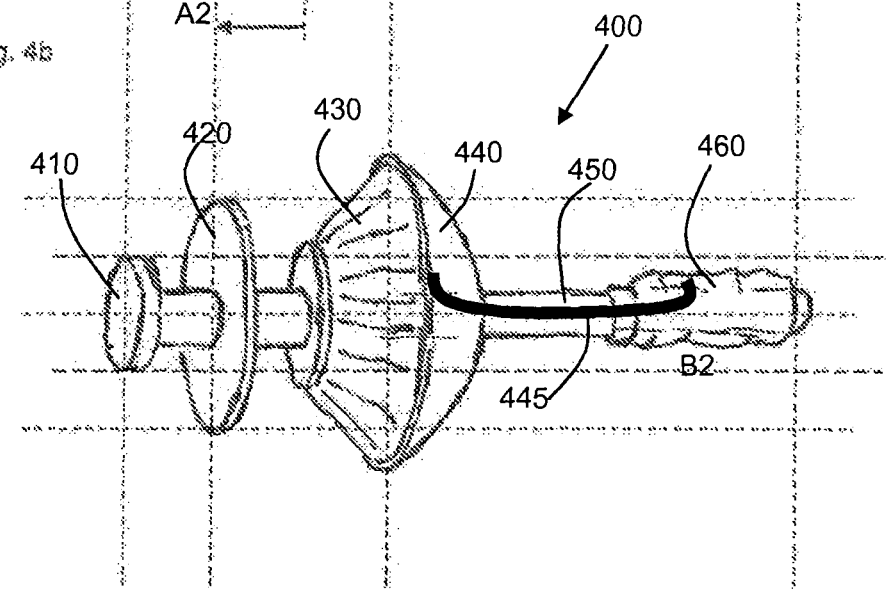

FIGS. 4a and 4b illustrate an earplug 400 including an inflatable element 460 attached to a reservoir (e.g., a chamber enclosed by an elastic membrane 430 and a stop flange body 440) and a stent 450, where an elastic membrane 430 provides a pressurizing force in accordance with at least one exemplary embodiment. FIG. 4a illustrates the earplug 400 with an inflated B1 inflation element 460. FIG. 4b illustrates a deflated B2 inflation element 460. For example when a moveable plate 420 in a first position A1 is pulled to position A2, fluid from the inflated inflation element 460 flows into the reservoir via an inflation channel 445, where the elastic membrane 430 provides a restoring and in this example a pressurizing force. In the operation of the exemplary embodiment a thumb can be placed on knob 410 while a finger pulls moveable plate 420.

FIGS. 5a and 5b illustrate an earplug 500 including an inflatable element 560 attached to a reservoir 530 and a stent 550, using a pinchable resilient member 520 to provide a pressurizing force in accordance with at least one exemplary embodiment. The resilient member 520 can have a portion that provides a restoring force equivalent to a spring constant 542. When the resilient member 520 is pinched reservoir 530 expands moving fluid from the inflation element 560 to the reservoir 530. When the resilient member is unpinched the resilient member 520 presses the reservoir 530 against the stop flange 540 where the fluid moves through the inflation channel 545 into the inflation element 560. A stent 550 with an anti-distal end 510 forms a core that the other elements can be anchored to.

Figure 6A:
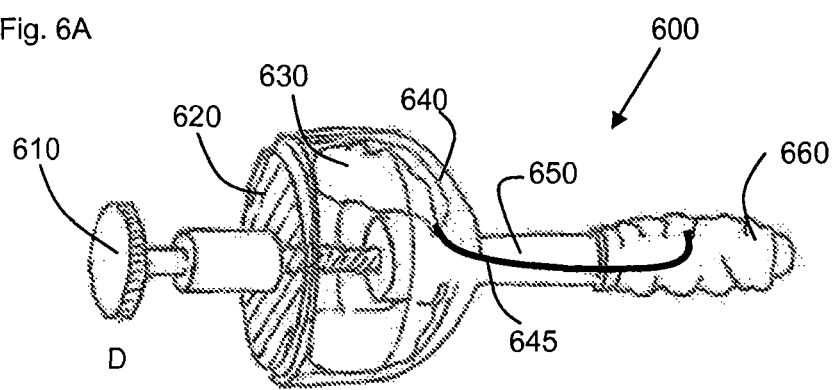
FIGS. 6A and 6B illustrate an earplug including an inflatable element attached to a reservoir and a stent, using a screwable plate to provide an adjustable pressurizing force in accordance with at least one exemplary embodiment.
Figure 6B:
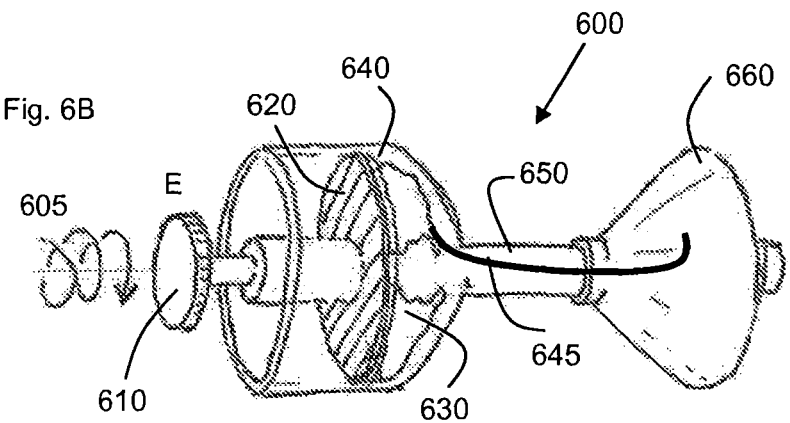

FIGS. 6A and 6B illustrate an earplug 600 including an inflatable element 660 attached to a reservoir 630 and a stent 650, using a screwable 605 plate 620 to provide an adjustable pressurizing force in accordance with at least one exemplary embodiment. When the knob 610 is moved from position D to position E, plate 620 presses the reservoir 630 against the stop flange 640 to move fluid through the inflation channel 645 into the inflation element 660. A user can use knob 610 to screw clockwise and anti-clockwise to adjust the deformation of reservoir 630 to move fluid in and out of inflation channel 645 to inflate the inflation element 660.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An earplug comprising:
    a distal end;
    an inflatable element coupled to the distal end; and
    a flexible anti-distal end coupled to the distal end, the inflatable element operatively attached to the anti-distal end by an inflation channel,
    where the anti-distal end includes a stop flange, a bladder serving as a reservoir and a pinchable resilient member, the bladder being disposed between the stop flange and the pinchable resilient member, the bladder coupled to the inflation channel, the pinchable resilient member expands the inflatable element to an adjustable pressure by having the pinchable resilient member providing a pressurizing force to maintain the expansion of the inflatable element and where the reservoir expands by moving fluid from the inflation element to the reservoir when pinching the pinchable resilient member.

2. The earplug according to claim 1, where the inflatable element is at least one balloon.

3. The earplug according to claim 2, where the inflatable element is pressurized with a gauge pressure between about 0.1 bar and about 0.4 bar.

4. The earplug according to claim 1, where the anti-distal end is configured to be deformed, to move the fluid into the inflatable element.

5. The earplug according to claim 4 where the fluid is air or other gas.

* * * * *